United States Patent [19]

Massardo et al.

[11] Patent Number: 4,594,352
[45] Date of Patent: Jun. 10, 1986

[54] ALKYNYL CONTAINING BENZOYL-UREAS EXERTING AN INSECTICIDAL ACTIVITY

[75] Inventors: Pietro Massardo, Milan; Franco Bettarini; Gabriele Giovarruscio, both of Novara; Paolo Piccardi; Franca Reggiori, both of Milan; Vincenzo Caprioli, San Martino; Angelo Longoni, Milan, all of Italy

[73] Assignee: Montedison S.p.A., Milan, Italy

[21] Appl. No.: 601,923

[22] Filed: Apr. 19, 1984

[30] Foreign Application Priority Data

Apr. 22, 1983 [IT] Italy ................ 20745 A/83

[51] Int. Cl.[4] ................ C07D 213/75; C07C 127/22; A61K 31/44; A61K 31/17
[52] U.S. Cl. ................ 514/332; 514/335; 514/344; 514/346; 514/353; 514/357; 514/596; 514/597; 514/598; 514/522; 546/261; 546/264; 546/265; 546/286; 546/287; 546/288; 546/289; 546/291; 546/292; 546/306; 546/330; 546/332; 564/44; 558/417
[58] Field of Search ................ 546/306, 267, 330, 332, 546/261, 291, 292, 286, 287, 288, 289, 265, 306, 264; 564/44; 424/263, 322; 260/465 D; 514/332, 346, 335, 353, 344, 357, 522, 596, 597, 598

[56] References Cited

U.S. PATENT DOCUMENTS 4,321,276  3/1982  Ehrenfreund et al. ........ 564/44

FOREIGN PATENT DOCUMENTS 123903  9/1981  Japan .

Primary Examiner—Henry R. Jiles
Assistant Examiner—Dale A. Bjorkman

[57] ABSTRACT

There are described compounds of formula:

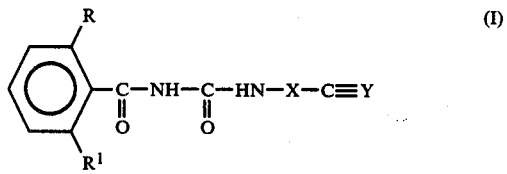

in which
one of R and $R^1$ is F or Cl and the other is H, F or Cl;
X is a 1,4-phenylene or pyridyl bound in positions 2 and 5, optionally substituted;
Y is a phenyl, 2- or 3-pyridyl, optionally substituted.

The compounds of formula I are endowed with a high insecticide activity which is mainly directed against insect larvae and eggs.

11 Claims, No Drawings

ALKYNYL CONTAINING BENZOYL-UREAS EXERTING AN INSECTICIDAL ACTIVITY

THE PRESENT INVENTION

This invention relates to benzoyl-urea derivatives having insecticide activity and, more particularly, it relates to derivatives of 1-benzoyl-3-aryl-urea which are particularly active against eggs and larvae of insects harmful in the agrarian and civil field, and to the use thereof.

This invention also relates to a process for synthesizing said ureas and to some new intermediates for the synthesis.

Various derivatives of 1-benzoyl-3-aryl-urea endowed with insecticide activity are already known.

Among these, the first product in commerce is Diflubenzuron, a trade designation for the compound 1-(2,6-difluorobenzoyl)-3-(4-chlorophenyl)-urea described in U.S. Pat. No. 3,993,908 (U.S. Phillips Corporation).

However, since Diflubenzuron contains the unit of 4-chloro-aniline in the molecule, it is suspected of being cancerogenic [European Chem. News 6 (16) 29 (1978)].

Among the various 1benzoyl-3-aryl-urea derivatives endowed with an insecticide activity mentioned in literature there may be cited benzoyl-phenyl-urea substituted in the phenyl radical with an ethynyl, which are described in European patent application No. 38,766 (Ciba-Geigy).

We have now found new derivatives of 1-benzoyl-3-aryl-urea, which are the object of the present invention, having the general formula:

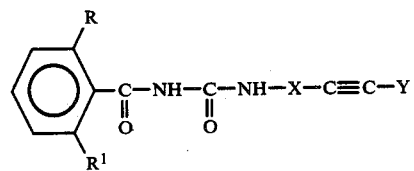

(I)

in which:
one of R and $R^1$ is a fluorine or chlorine atom and the other is an atom of hydrogen, of fluorine or of chlorine, X is a 1,4-phenylene or a pyridyl bound in position 2 to group NH and in position 5 to group —C≡C— or vice versa, said 1,4-phenylene or pyridyl groups being optionally substituted by one or two substituents selected from among atoms of fluorine and chlorine, groups $CF_3$, $OCF_3$, $OCHF_2$, CN, $N(R^2)_2$ ($R^2$=alkyl $C_1$-$C_4$), alkyl $C_1$-$C_4$, alkoxy $C_1$-$C_4$, alkylthio $C_1$-$C_4$;

Y is a phenyl or a 2- or 3-pyridyl, said phenyl or pyridyl groups being optionally substituted by from 1 to 4 substituents selected from fluorine and chlorine atoms, groups $CF_3$, $OCF_3$, $OCHF_2$, $NO_2$, CN, $N(R^2)_2$ ($R^2$=alkyl $C_1$-$C_4$), alkyl $C_1$-$C_4$, alkoxyl $C_1$-$C_4$, alkylthio $C_1$-$C_4$, alkenyl $C_2$-$C_5$, alkenyloxy $C_2$-$C_5$, alkenylthio $C_2$-$C_5$, alkylcarbonyl or alkoxycarbonyl having 1 to 4 carbon atoms in the alkyl moiety, aminocarbonyl, or dialkylaminocarbonyl having from 1 to 4 carbon atoms in each alkyl substituent.

The compounds of formula I are endowed with an insecticide activity and are suitable for use in the agrarian and civil field against infestations due to insects.

Examples of compounds of formula I are the compounds having the following formulae:

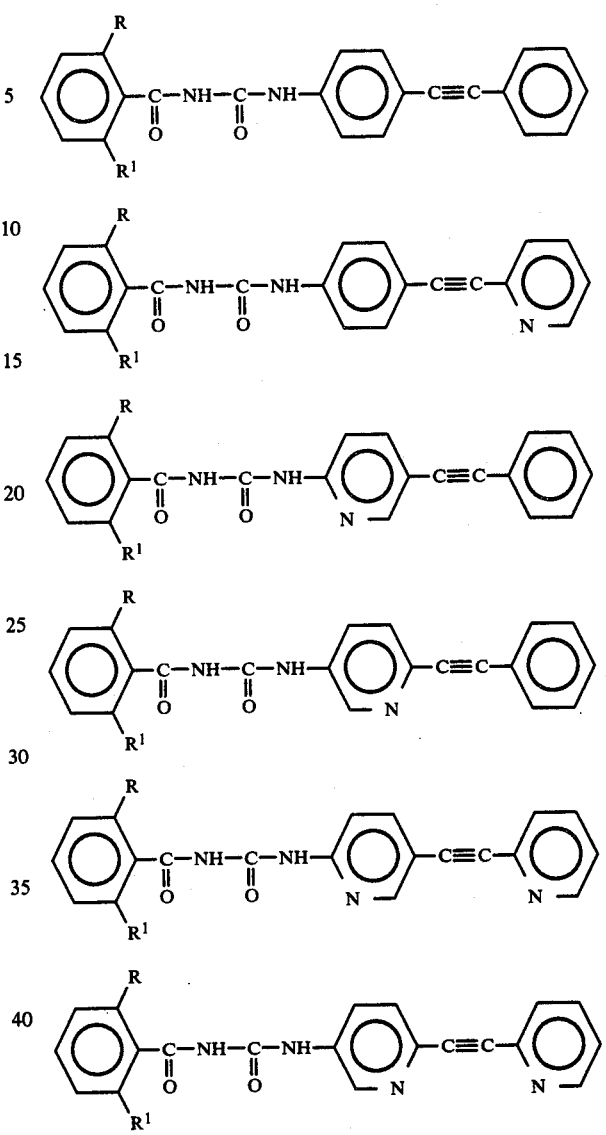

(in which R and $R^1$ have the same meaning as in formula I) and the corresponding derivatives in which the phenyl and/or pyridyl nucleus is substituted in the same manner as indicated for formula I groups (groups X and Y).

The compounds of formula I are prepared by reacting a benzoyl-isocyanate of formula (II):

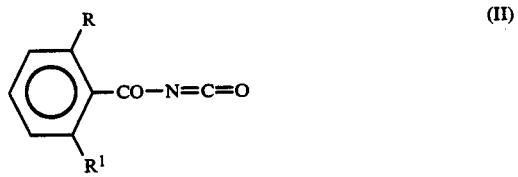

(II)

(in which R and $R^1$ are the same as specified for formula I) with an aromatic amine of formula (III):

$H_2N$—X—C≡C—Y    (III)

(in which X and Y are the same as indicated for formula I).

The reaction does not require the presence of a catalyst and is carried out in an inert solvent at a temperature ranging from 0° C. to the boiling temperature of the reaction mixture.

Suitable solvents are aromatic hydrocarbons, chlorinated hydrocarbons, ethers, ketones and acetonitrile.

The benzoyl-isocyanates of formula II are known compounds which are readily prepared and in some cases commercially available.

The amines of formula III are new compounds and, as such, constitute a further object of the invention.

They are prepared by reacting an aromatic amine (aniline, 2- or 3-amino-pyridine, optionally substituted by the substituents of group X in formula III), substituted in para position with respect to the amino group by an atom of bromine or of iodine, by an aryl-acetylene (in which the aryl is group Y of formula III).

For the sake of simplicity, there is described in detail the preparation of a compound of formula III in which X is a non-substituted 1,4-phenylene and Y is an optionally substituted phenyl, i.e., a compound having the formula:

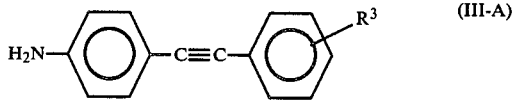
(III-A)

in which $R^3$ is a hydrogen atom or one of the substituents listed in formula I as possible substituents of group Y. It is to be understood that the synthesis method described hereinbelow is applicable in like manner to the synthesis of all the compounds of formula III.

The preparation of compound III-A is accomplished by reacting a 4-halogen-substituted aniline (IV) with an optionally substituted phenylacetylene (V) according to the reaction:

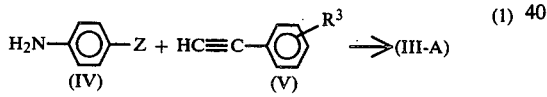
(1)

in which Z is a bromine atom or preferably an iodine atom and $R^3$ has the same meanings as indicated for formula III-A.

Reaction 1 is carried out in a basic solvent, for example triethylamine, at a temperature ranging from the room temperature to the boiling temperature of the reaction mixture, in an inert gas atmosphere and in the presence of catalytic amounts of palladium-bis-triphenylphosphine dichloride, $Pd[C_6H_5)_3P]_2Cl_2$, and optionally of cupreous iodide (CuI).

Similar reactions, but on different substrates are described in Italian Pat. No. 1,006,879 (Montedison S.p.A.), in Tetrahedron Letters 50, 4467 (1975); Journal of Organometallic Chemistry 93, 253 (1975) and 93, 259 (1975).

While 4-bromo or 4-iodo-aniline is a known and easily available compound, aryl-acetylene of formula V, depending on the meanings of substituent $R^3$, may require a specific preparation.

Different modalities may be followed for preparing the compounds of formula V which directly derive from reactions known in the chemistry of the aryl-acetylenes.

Among these modalities there may be cited:

a. the reaction between acetylene and a halobenzene (bromo- or preferably iodo-benzene) optionally substituted.

Instead of acetylene as such it is preferable to use a protected acetylene in the form of trimethyl-ethylnyl-silane, or in the form of 1,1-dimethyl-propargyl alcohol. The reaction with halobenzene is followed by the release of the alkyne from the protective group.

An example of a reaction scheme is the following:

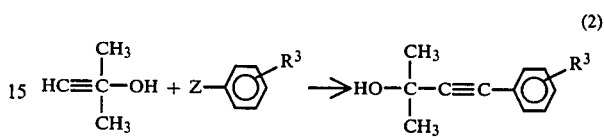
(2)

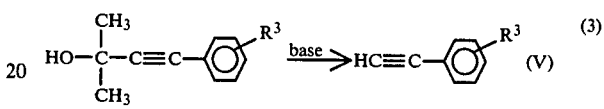
(3)

Reaction 2 is conducted according to the operating modalities described for reaction 1. Reactions analogous to reactions 2 and 3 have been described in Synthesis 364 (1981).

b. The bromination and double dehydrobromination reaction conducted on a styrene of formula:

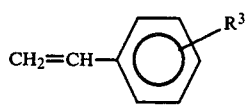

c. the reaction between tetrabromomethane ($CBr_4$) and a benzaldehyde of formula:

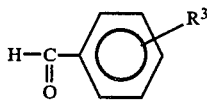

in the presence of triphenylphosphine and subsequent double dehydrobromination with lithiobutyl of the obtained 2,2-dibromostyrene.

Owing to the simplicity of the operating modalities, to the best yields and the easy availability of the starting products it is generally preferred to prepare the phenylacetylenes of formula V according to the reactions indicated at point a.

As will be apparent to those skilled in the art, the amines of formula III can be prepared according to alternative synthesis modalities, such as e.g., the reactions reported hereinafter:

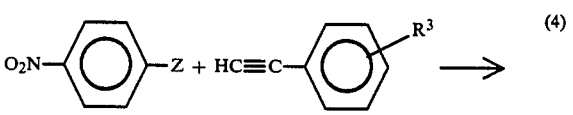
(4)

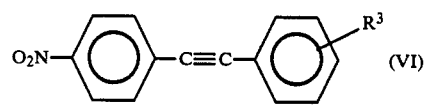
(VI)

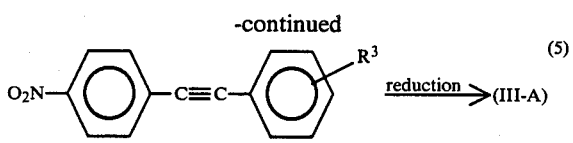

Reaction 4 is analogous to reaction 1, but is carried out on 4-halo-nitrobenzene instead of on 4-halo-aniline of formula IV. The nitro-derivative VI is then reduced to the corresponding aniline (reaction 5) according to known techniques, for example with sodium sulphite or tin chloride.

As an alternative, it is possible to adopt the same modalities of reaction 1 but on substrates having the functional groups inverted, and namely according to the following reaction:

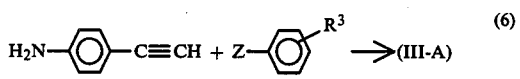

or also on the corresponding 4-nitrophenyl-acetylene and reduction of the resulting nitroderivative, similar to product (VI) of reaction 4.

The preparation of the anilines of formula III can be accomplished, also, by reacting a 4-bromo- or 4-iodo-aniline with a copper acetylide of formula:

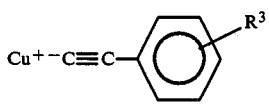

Analogous reactions but on different substrates have been described in the literature, for example by C. E. Castro et al, Journal Org. Chem. 31, 4071 (1966).

As far as concerns the preparation of benzoyl-ureas, it is known in the literature that the synthesis can also be carried out by reacting an aryl-isocyanate with a benzamide.

In the specific case relating to the preparation of the compounds of formula I, this reaction is represented by the following equation:

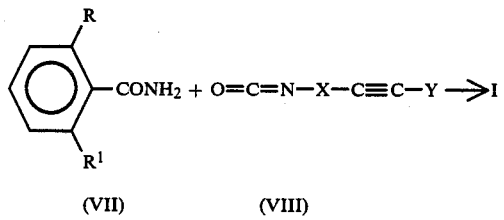

In principle, it is certainly possible to prepare the compounds of formula I according to reaction 7, which is experimentally carried out in like manner as the condensation between benzoyl-isocyanate (II) and the aromatic amine (III).

However, the preparation of the isocyanates of formula (VIII) must be accomplished by reaction of an amine of formula (III) with phosgene. This aspect, combined with the fact that the benzoyl-isocyanates of formula (II) are available like the amides of formula (VII), leads to general preference for the synthesis method previously described rather than the method of reaction 7.

As already mentioned, the compounds of formula I are endowed with a high insecticide activity which is chiefly exerted against insect larvae and eggs.

Among the insects it is possible to fight with the compounds of formula I, are, in particular, those belonging to the Diptera, Lepidoptera and Coleoptera orders.

These orders include several species which are important due to their harmfulness in the agrarian, forestal, civil and veterinary fields. Therefore, the compounds of formula I are suitable for various uses such as, for example, the defense of the agricultural cultivations from infestations caused by phytophagous insects, the protection of places infested by flies and mosquitoes, the protection of breeding animals against some cattle parasites, etc.

The compounds of formula I exhibit, moreover, a collateral acaricide activity.

For practical uses, the compounds of general formula I can be employed as such or, more advantageously, in the form of compositions containing, besides one or more of the compounds of formula I as an active substance, also solid or liquid inert vehicles and optionally other additives. According to the usual formulation practice, the compositions may be in the form of wettable powders, emulsifiable concentrates and the like.

The amount of active substance in the compositions varies over a wide range (1–95% by weight) depending on the composition type and on the use for which it is intended.

If required by particular situations or with a view to extending the action range, it is possible to add to the compositions other active substances, such as e.g., other insecticides or acaricides.

The amount of active substance (compound of formula I) to be distributed for the insecticide treatments depends on various factors, such as, for example, the type and degree of the infestation, the substrate in which the infestation is present (agrarian cultivations, stretches of water and waterways, organic substrates of various nature), the type of composition utilized, climatic and environmental factors, available applicative means, etc. In general, amounts of active substance from 0.01 to 1 kg/ha are sufficient for a good disinfestation.

The following non-limiting examples are given with a view to illustrating the invention in more detail.

EXAMPLE 1

This example relates to the preparation of arylacetylene derivatives and has the main object of showing the methodology for preparing said compounds—a few of which are already described in the literature—according to an adaptation of the procedure described in Synthesis 364 (1981).

Preparation of 4-chloro-phenylacetylene:

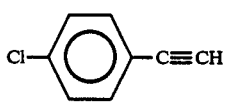

There was prepared a mixture consisting of:
9.5 g (0.04 moles) of 4-chloro-iodobenzene;
4.2 g (0.05 moles) of 1,1-dimethyl-propargyl alcohol

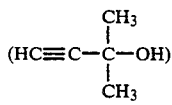

0.3 g of palladium-bis-triphenylphosphine dichloride Pd[(C₆H₅)₃P]₂Cl₂;
100 ml of triethylamine.

Nitrogen was caused to bubble into said mixture for about 15 minutes.

While maintaining the mixture in a nitrogen atmosphere, 180 mg of cupreous iodide were added.

An almost immediate formation of a precipitate was observed.

It was stirred at room temperature for about 12 hours, diluted with ethyl ether (200 ml) and filtered.

Almost all the solvent was removed from the filtrate by evaporation at reduced pressure, and the residue was diluted with 150 ml of toluene.

2.5 g of ground NaOH were added to the resulting solution, and it was heated to reflux temperature for 4 hours.

After hot filtration, the solvent was removed from the filtrate by evaporation under reduced pressure.

4.6 g of 4-chloro-phenylacetylene in the form of a waxy solid were thus obtained.

1H-NMR. (CDCl₃, TMS); δ(ppm); 2.3 (s, 1H); 7.3 (m, 4H, aromatic protons); s=singlet, m=multiplet.

By operating in the manner described, there were prepared the aryl-acetylenes of formula:

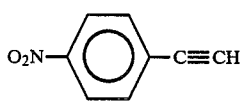

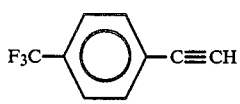

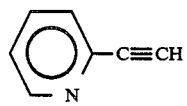

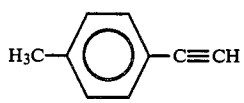

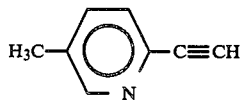

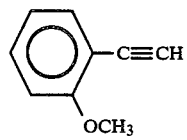

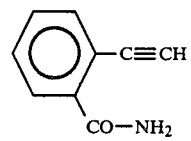

EXAMPLE 2

Preparation of 4-[(4-chlorophenyl)-ethynl]-aniline

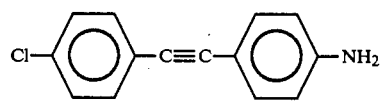

There was prepared a mixture consisting of:
4.4 g (0.032 moles) of 4-chloro-phenylacetylene;
7.0 g (0.032 moles) of 4-iodo-aniline;
0.2 g of Pd[(C₆H₅)₃P]₂Cl₂;
80 ml of triethylamine.

Nitrogen was caused to bubble into the mixture for about 15 minutes.

180 mg of cupreous iodide were added to the mixture, kept under stirring in a nitrogen atmosphere, and the whole was maintained under stirring at room temperature for about 12 hours.

The reaction mixture was then diluted with ethyl ether (200 ml) and filtered.

The solvent was removed from the filtrate by evaporation under reduced pressure.

Thus, 5 g of the desired product in the form of a thick liquid were obtained as residue.

Elemental analysis: C₁₄H₁₀NCl: C (%) calculated 73.85, found 73.7; H (%) calculated 4.39, found 4.4; N (%) calculated 6.15, found 6.2; Cl (%) calculated 15.60, found 15.4.

By operating in the manner described hereinabove, starting from 4-iodo-aniline and from the suitable arylacetylene, the aromatic amines having the following formulae were prepared:

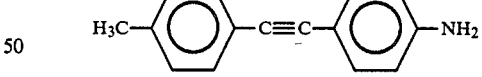

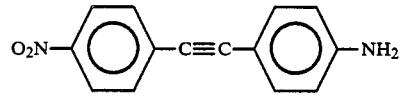

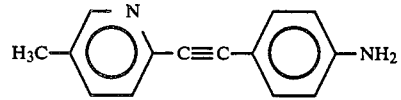

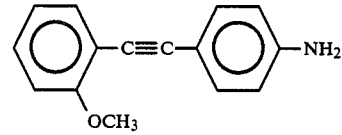

-continued

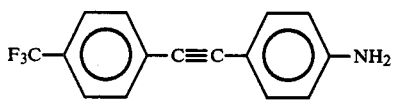

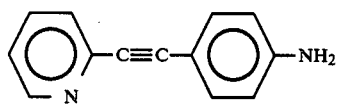

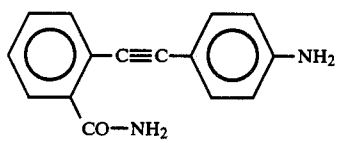

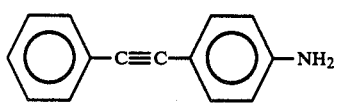

EXAMPLE 3

Preparation of
1-(2-chloro-benzoyl)-3-[4-(4-chlorophenyl)ethylnyl]-phenylurea (Compound No. 1)

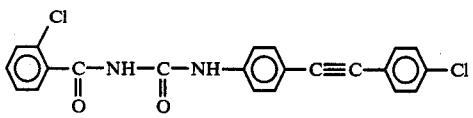

A solution of 1.7 g of 2-chloro-benzoyl-isocyanate

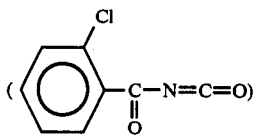

in 20 ml of anhydrous ethyl ether was added dropwise to a solution of 2.1 g of 4-[(4-chlorophenyl)-ethynyl]-aniline

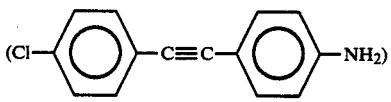

in 20 ml of dry ethyl ether maintained in a nitrogen atmosphere at a temperature of 0° C.

On conclusion of the addition, the mixture was heated at a reflux for 2 hours.

A solid separated, which was gathered by filtration, washed with cold ethyl ether and dried.

2.4 g of the desired product (M.P.=210°-212° C.) were obtained.

EXAMPLE 4

By operating in the manner described in Example 3, the compounds of formula I indicated in the following Table 1 were prepared.

TABLE 1

Compounds of formula (a)

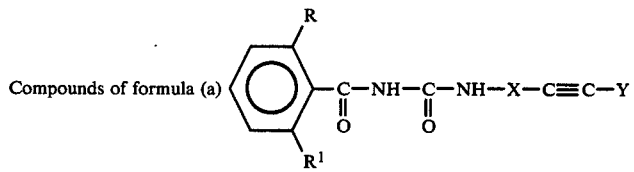

| Compound No. | R (or R¹) | R¹ (or R) | —X— | —Y— | M.P. (°C.) (b) |
|---|---|---|---|---|---|
| 1 (c) | Cl | H | ⌬— | ⌬—Cl | 210–212 |
| 2 | Cl | H | ⌬— | ⌬—NO₂ | 216–7 |
| 3 | Cl | H | ⌬— | ⌬(N) | 177–8 |
| 4 | Cl | H | ⌬— | ⌬—OCH₃ | 225–6 |

TABLE 1-continued

Compounds of formula (a)

$$\text{R-C}_6\text{H}_3(\text{R}^1)\text{-C(O)-NH-C(O)-NH-X-C} \equiv \text{C-Y}$$

| Compound No. | R (or R¹) | R¹ (or R) | —X— | —Y— | M.P. (°C.) (b) |
|---|---|---|---|---|---|
| 5 | Cl | H | –C₆H₄– | –C₆H₄–CF₃ | 131–2 |
| 6 | Cl | H | –C₆H₄– | –C₆H₄–CH₃ | 155–6 |
| 7 | Cl | H | –C₆H₄– | pyridyl–CH₃ | 148–9 |
| 8 | Cl | H | –C₆H₄– | –C₆H₅ | 138–9 |
| 9 | Cl | H | –C₆H₄– | –C₆H₃(Cl)(Cl) (3,4-diCl) | 206–208 |
| 10 | Cl | H | –C₆H₄– | –C₆H₃(Cl)(Cl) (3,5-diCl) | 216–218 |
| 11 | Cl | H | pyridyl | –C₆H₅ | 182–184 |
| 12 | Cl | Cl | pyridyl | –C₆H₅ | 190–192 |
| 13 | Cl | H | –C₆H₄– | –C₆H₃(Cl)(Cl) (2,4-diCl) | 198–200 |
| 14 | Cl | H | pyrimidyl | –C₆H₄–Cl | 192–194 |

TABLE 1-continued

Compounds of formula (a) 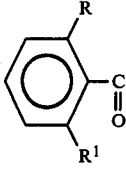

| Compound No. | R (or R¹) | R¹ (or R) | —X— | —Y— | M.P. (°C.) (b) |
|---|---|---|---|---|---|
| 15 | Cl | H | 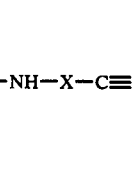 | 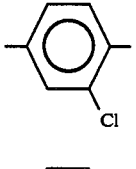 | 178–180 |
| 16 | Cl | H | 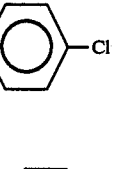 | 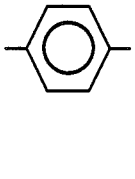 | 170–172 |
| 17 | Cl | H | 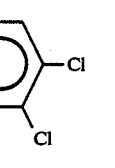 | 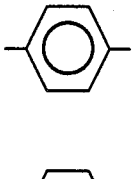 | 189–190 |
| 18 | Cl | H | 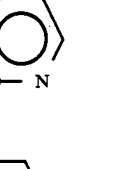 | 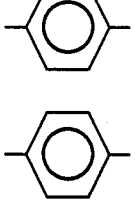 | 186–188 |
| 19 | Cl | H | 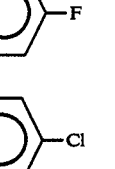 |  | 201–203 |
| 20 | F | F |  |  | 215–217 |
| 21 | Cl | H |  |  | 196–197 |
| 22 | Cl | H | 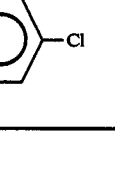 | | 208–210 |

EXAMPLE 5

Determination of the insecticide activity

Test 1

Activity on *Spodoptera littoralis* (Lepidoptera) larvae.

1a. Immediate residual activity.

Tobacco leaves were treated by mechanical spraying with a hydroacetonic solution of the product being tested at 10% by volume of acetone and containing a surfactant.

After complete evaporation of the solvents, the leaves were infested with second age larvae of the Lepidopter. The infested leaves were kept in a properly conditioned ambient for the entire duration of the test.

In the same manner there were infested and preserved tobacco leaves treated only with a hydroacetonic solution at 10% of acetone and with the surfactant, to be used as a check.

10 days after the infestation and after having renewed the treated substrate at least once, the dead larvae were counted with respect to the check.

1b. Activity by topical application.

Lepidopter larvae at the beginning of the last age were treated, by topical application onto the first urosternites, with a hydroacetonic solution of the product being tested (10% by volume of acetone). As a check, another group of larvae of the same age was analogously treated with a hydroacetonic solution not containing any active substance. The results were determined by counting the number of dead larvae and pupae and of adults normally emerged from the cocoon when in the check the emergence from the cocoon was concluded.

The activity is expressed as percent ratio of dead individuals in respect of the total number of treated larvae.

Test 2

Activity on *Aedes aegypti* (Diptera) larvae.

Spring water (297 ml) was mixed with an acetonic solution (3 ml) of the product being tested in a proper concentration. Into the resulting solution, 25 4-day old Dipter larvae were introduced and suitably fed. As a check, other larvae were introduced into a hydroacetonic solution (3 ml of acetone, 297 ml of spring water) without any active substance.

Every 2-3 days there was determined the number of dead larvae and pupae and of adults normally emerged from the cocoon, until conclusion of the emergence from the cocoon of the insects in the check.

The activity of the product being tested is expressed as percent ratio of dead individuals in respect of the total number of treated individuals.

The insecticide activity in the tests is expressed according to the following scale of values:

5 = complete activity (98–100% of mortality)
4 = high activity (80–97% of mortality)
3 = fairly good activity (60–79% of mortality)
2 = sufficient activity (40–59% of mortality)
1 = poor activity (20–39% of mortality)
0 = negligible activity or no activity (0–19% of mortality).

The data relating to the insecticide activity at the indicated doses, expressed by means of the scale of values reported, are recorded in the following Table 2.

TABLE 2

| Compound No. (See Table 1) | Insecticide Activity | | | |
|---|---|---|---|---|
| | Test 1-a Dose: 0.001% | Test 1-b Dose: 2 γ/ins. | Dose: 0.2 γ/ins. | Test 2 Dose: 0.01 ppm |
| 1 | 5 | 5 | 5 | 5 |
| 2 | — | 5 | 5 | 5 |
| 3 | 5 | 5 | 5 | 5 |
| 4 | — | 5 | 5 | 5 |
| 5 | 5 | 5 | 5 | 5 |
| 6 | 5 | 5 | 5 | 5 |
| 7 | 5 | 5 | 5 | 5 |

TABLE 2-continued

| Compound No. (See Table 1) | Insecticide Activity | | | |
|---|---|---|---|---|
| | Test 1-a Dose: 0.001% | Test 1-b Dose: 2 γ/ins. | Dose: 0.2 γ/ins. | Test 2 Dose: 0.01 ppm |
| 8 | 4 | 5 | 4 | 5 |
| 9 | 4 | — | — | 2 |
| 10 | 5 | — | — | 2 |
| 11 | 4 | — | — | 3 |
| 12 | 4 | — | — | 4 |
| 13 | 3 | — | — | 1 |
| 14 | 2 | — | — | 1 |
| 15 | 5 | — | — | 2 |
| 16 | 5 | — | — | 3 |
| 17 | 4 | — | — | 5 |
| 18 | 4 | — | — | 5 |
| 19 | 5 | — | — | 5 |
| 20 | 5 | — | — | 5 |
| 21 | 3 | — | — | 4 |
| 22 | 3 | — | — | 1 |
| CHECK* | 1 | 3 | 0 | 1 |

*As a check there was used the compound 1-(2-chlorobenzoyl)-3-(4-ethynylphenyl)-urea of formula:

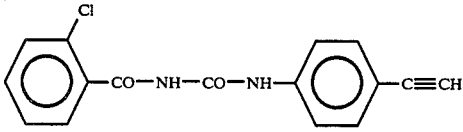

disclosed in European patent application No. 38,766.

What is claimed is:

1. A compound of formula

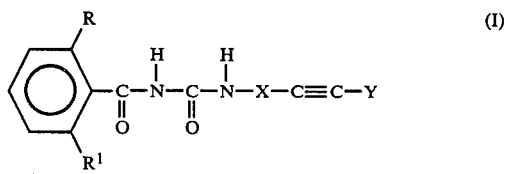

in which
one of R and $R^1$ is fluorine or chlorine and the other is hydrogen, fluorine or chlorine;
X is selected from the group consisting of 1,4-phenylene and pyridyl bound in position 2 to the NH group and in position 5 to the —C≡C— group or vice versa; the 1,4 phenylene substituted by one to two substituents selected from the group consisting of fluorine, chlorine, $CF_3$, $OCF_3$, $OCHF_2$, CN, $N(R^2)_2$ ($R^2$ is $C_1$-$C_4$ alkyl), $C_1$-$C_4$ alkyl, $C_1$-$C_4$ alkoxy, $C_1$-$C_4$ alkylthio; and the pyridyl substituted by one or two substituents selected from the group consisting of fluorine, chlorine, $CF_3$, $OCF_3$, $OCHF_2$, CN, $N(R^2)_2$ ($R^2$ is $C_1$-$C_4$ alkyl), $C_1$-$C_4$ alkyl, $C_1$-$C_4$ alkoxy, $C_1$-$C_4$ alkylthio;
Y is selected from the group consisting of phenyl, 2-pyridyl, 3-pyridyl, phenyl substituted by 1 to 4 substituents selected from the group consisting of fluorine, chlorine, $CF_3$, $OCF_3$, $OCHF_2$, $NO_2$, CN, $N(R^2)_2$ ($R^2$ is $C_1$-$C_4$ alkyl), $C_1$-$C_4$ alkyl, $C_1$-$C_4$ alkoxy, $C_1$-$C_4$ alkylthio, $C_2$-$C_5$ alkenyl, $C_2$-$C_5$ alkenyloxy, $C_2$-$C_5$ alkenylthio, alkylcarbonyl having 1 to 4 carbon atoms in the alkyl moiety, alkoxycarbonyl having 1 to 4 carbon atoms in the alkyl moiety, aminocarbonyl, and dialkylamino carbonyl having 1 to 4 carbon atoms in each alkyl substituent; and the pyridyl substituted by 1 to 4 substituents selected from the group consisting of fluorine, chlorine, $CF_3$, $OCF_3$, $OCHF_2$, $NO_2$, CN, $N(R^2)_2$ ($R^2$ is $C_1$-$C_4$ alkyl), $C_1$-$C_4$ alkyl, $C_1$-$C_4$ alkoxy, $C_1$-$C_4$ alkylthio, $C_2$-$C_5$ alkenyl, $C_2$-$C_5$ alkenyloxy, $C_2$-$C_5$ alkenylthio, alkylcarbonyl having 1 to 4 carbon atoms in the alkyl moiety, alkoxycarbonyl having 1 to 4 carbon atoms in the alkyl moiety, aminocarbonyl, and dialkylaminocarbonyl having 1 to 4 carbon atoms in each alkyl substituent.

2. A compound according to claim 1, having the formula:

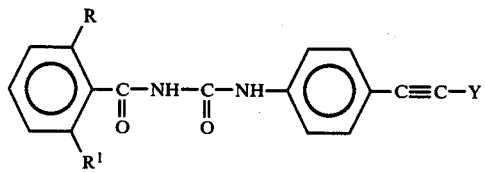

in which R, R$^1$ and Y have the same meaning as in formula I.

3. A compound according to claim 2, in which one of R and R$^1$ is a chlorine atom and the other is a hydrogen atom.

4. A compound according to claim 3, in which substituent Y is selected from the group consisting of 4-chlorophenyl, 4-nitro-phenyl, 2-pyridyl, 2-aminocarbonyl-phenyl, 2-methoxy-phenyl, 4-trifluoromethyl-phenyl, 4-methyl-phenyl, 5-methyl-2-pyridyl and phenyl.

5. A compound according to claim 1 and having the formula:

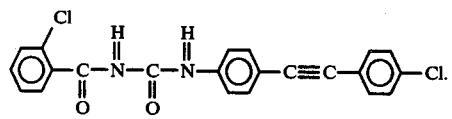

6. A compound according to claim 1 and having the formula:

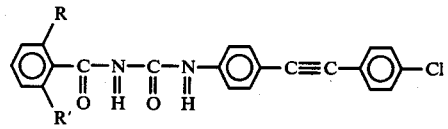

in which one of R and R' is Cl and the other is H.

7. A compound according to claim 1 and having the formula:

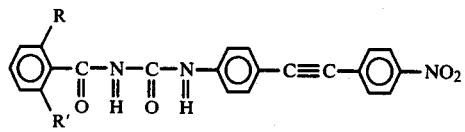

in which one of R and R' is Cl and the other is H.

8. A compound according to claim 1 and having the formula:

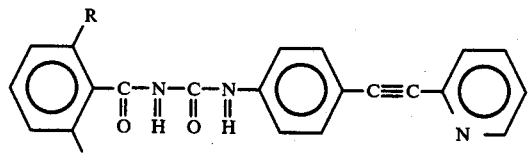

in which one of R and R' is Cl and the other is H.

9. A compound according to claim 1 and having the formula:

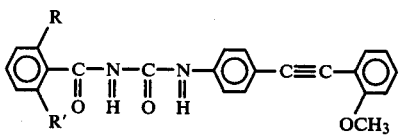

in which one of R and R' is Cl and the other is H.

10. A compound according to claim 1 and having the formula:

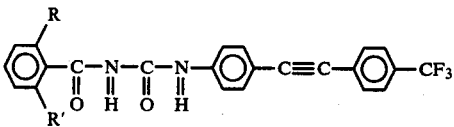

in which one of R and R' is Cl and the other is H.

11. A method for combatting infestations of harmful insects in the agrarian and civil fields, consisting in applying to said insects or to areas to be protected from said insects, an insecticidally effective amount of at least one compound according to claim 1.

* * * * *